United States Patent [19]
Delaplane et al.

[11] Patent Number: 6,009,872
[45] Date of Patent: Jan. 4, 2000

[54] RETENTION SYSTEM FOR ANTI-DISCONNECT APPARATUS AND METHOD, FOR BREATHING SYSTEMS

[75] Inventors: David Delaplane; Robert Bohning, both of Simi Valley, Calif.

[73] Assignee: Hammer-Plane, Inc., Simi Valley, Calif.

[21] Appl. No.: 09/243,076

[22] Filed: Feb. 2, 1999

Related U.S. Application Data

[63] Continuation-in-part of application No. 09/080,185, May 18, 1998, which is a continuation-in-part of application No. 09/010,883, Jan. 22, 1998.

[51] Int. Cl.⁷ .................................................. A61M 16/00
[52] U.S. Cl. ............ 128/207.17; 128/912; 128/DIG. 26
[58] Field of Search ........................ 128/200.26, 207.14, 128/207.15, 207.17, 207.29, DIG. 26, 912

[56] References Cited

U.S. PATENT DOCUMENTS

| | | | |
|---|---|---|---|
| 1,592,345 | 7/1926 | Drager | 128/207.17 |
| 1,835,757 | 12/1931 | Burchett | 128/207.17 |
| 2,765,792 | 10/1956 | Nichols | 128/207.17 |
| 2,928,387 | 3/1960 | Layne | 128/201.19 |
| 3,039,469 | 6/1962 | Fountain | 128/200.26 |
| 3,086,529 | 4/1963 | Munz et al. | 406/203 |
| 3,146,778 | 9/1964 | Krawiec | 128/DIG. 26 |
| 3,236,236 | 2/1966 | Hudson | 128/207.17 |
| 3,535,719 | 10/1970 | Murcott | 5/424 |
| 3,602,227 | 8/1971 | Andrew | 128/207.17 |
| 3,688,774 | 9/1972 | Akiyama | 128/200.26 |
| 3,774,616 | 11/1973 | White et al. | 128/DIG. 26 |
| 3,927,676 | 12/1975 | Schultz | 128/207.17 |
| 3,946,742 | 3/1976 | Eross | 128/207.17 |
| 3,973,569 | 8/1976 | Sheridan et al. | 128/207.15 |
| 3,987,798 | 10/1976 | McGinnis | 128/DIG. 26 |
| 4,018,221 | 4/1977 | Rennie | 128/207.18 |
| 4,027,666 | 6/1977 | Marx | 602/62 |
| 4,088,136 | 5/1978 | Hasslinger et al. | 604/179 |
| 4,235,229 | 11/1980 | Ranford et al. | 128/207.17 |
| 4,246,897 | 1/1981 | Muto | 128/207.15 |
| 4,256,099 | 3/1981 | Dryden | 128/200.26 |
| 4,304,228 | 12/1981 | Depel | 128/200.26 |
| 4,313,437 | 2/1982 | Martin | 128/207.17 |
| 4,331,144 | 5/1982 | Wapner | 128/207.17 |
| 4,485,822 | 12/1984 | O'Connor et al. | 128/207.17 |
| 4,527,559 | 7/1985 | Roxburg et al. | 128/207.17 |
| 4,548,200 | 10/1985 | Wapner | 128/207.17 |
| 4,598,705 | 7/1986 | Lichtenberger | 128/200.26 |
| 4,641,646 | 2/1987 | Schultz et al. | 128/207.14 |
| 4,738,662 | 4/1988 | Kalt et al. | 604/180 |
| 4,838,867 | 6/1989 | Kalt et al. | 604/180 |
| 4,844,061 | 7/1989 | Carroll | 128/DIG. 26 |
| 4,848,331 | 7/1989 | Northway-Meyer | 128/200.26 |
| 4,906,234 | 3/1990 | Voychehovski | 604/79 |
| 5,000,741 | 3/1991 | Kalt | 128/207.17 |
| 5,009,227 | 4/1991 | Nieuwstad | 128/207.17 |
| 5,010,884 | 4/1991 | Van Derdoes et al. | 128/207.17 |
| 5,042,477 | 8/1991 | Lewis | 128/207.17 |
| 5,054,482 | 10/1991 | Bales | 128/207.14 |
| 5,056,515 | 10/1991 | Abel | 128/207.15 |
| 5,069,206 | 12/1991 | Crosbie | 128/207.17 |
| 5,101,822 | 4/1992 | Kimel | 128/207.14 |
| 5,123,410 | 6/1992 | Green et al. | 128/207.17 |
| 5,282,463 | 2/1994 | Hammersley | 128/207.15 |
| 5,357,952 | 10/1994 | Schuster et al. | 128/207.17 |
| 5,413,095 | 5/1995 | Weaver | 128/DIG. 26 |
| 5,471,980 | 12/1995 | Varner | 128/207.17 |
| 5,671,732 | 9/1997 | Bowen | 128/DIG. 26 |
| 5,782,236 | 7/1998 | Ess | 128/207.17 |

Primary Examiner—Aaron J. Lewis
Attorney, Agent, or Firm—William W. Haefliger

[57] ABSTRACT

A method of connecting flexible first band structure to a tracheostomy neck plate, the neck plate having a first wing projecting laterally, the method includes: providing first anchoring structure including a first clip connectable to the wing, the band structure connectible to the first anchor; the first anchor configured to be anchored to the neck plate via the clip and a first opening through the wing, and the first anchor having a first section offset relative to the clip; and providing a first lock in association with the section, for holding the anchor in anchored relation to the wing, and releasable to free the first anchor from the wing.

9 Claims, 3 Drawing Sheets

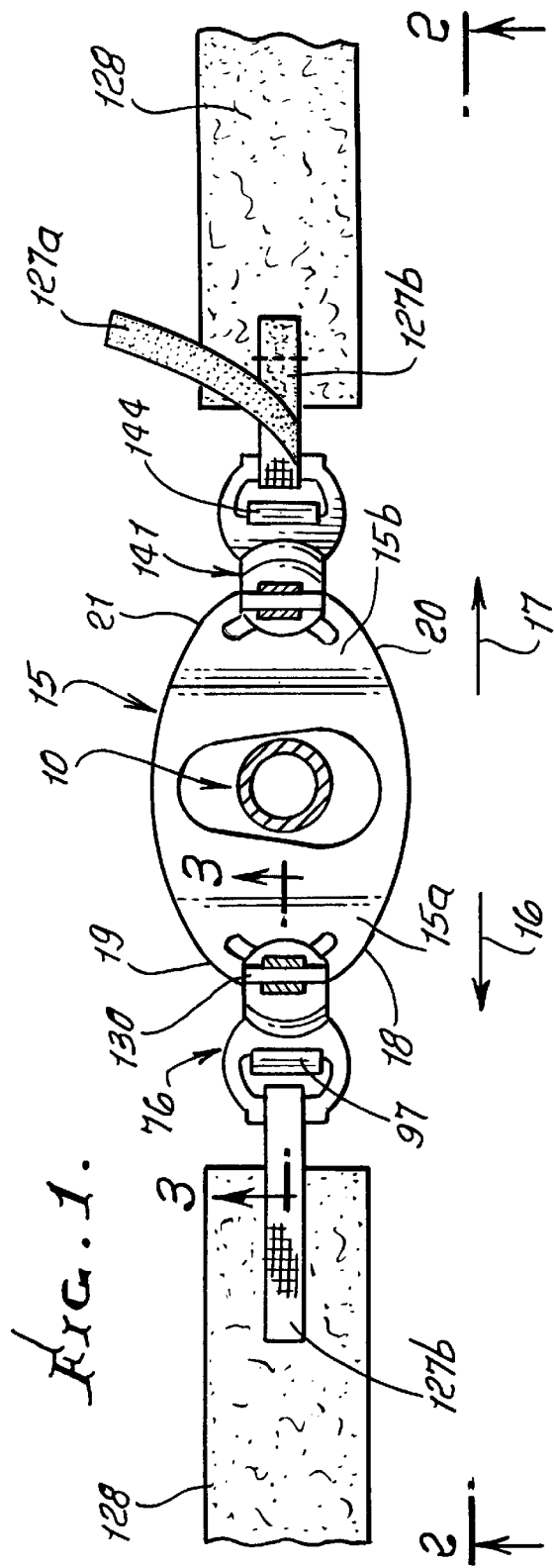
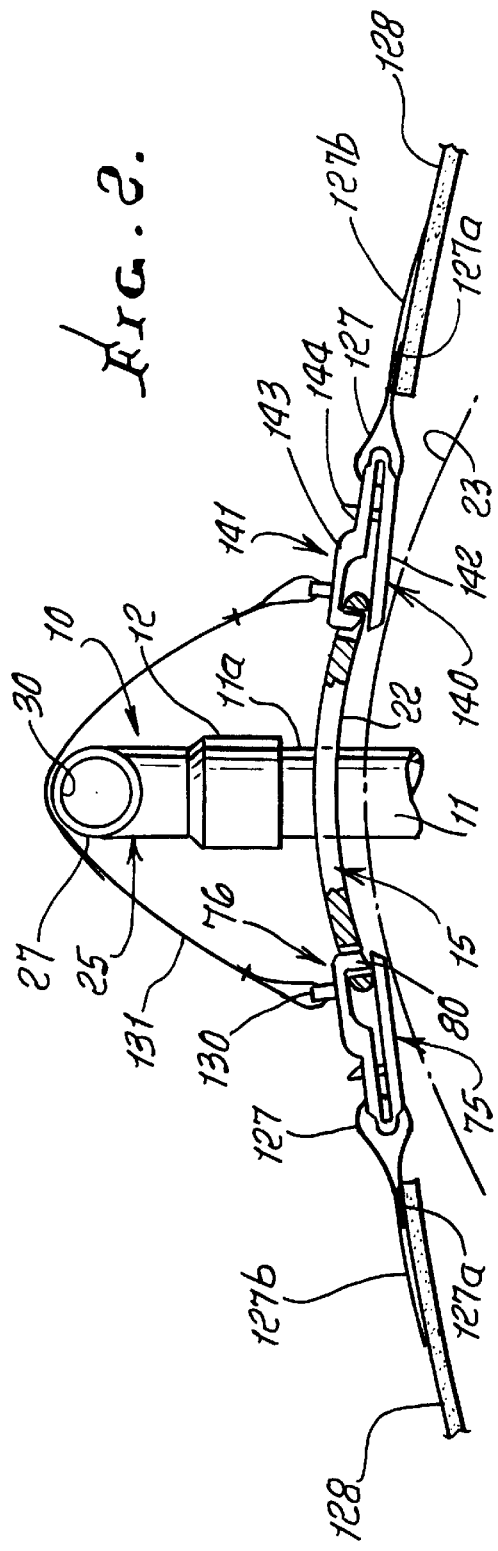

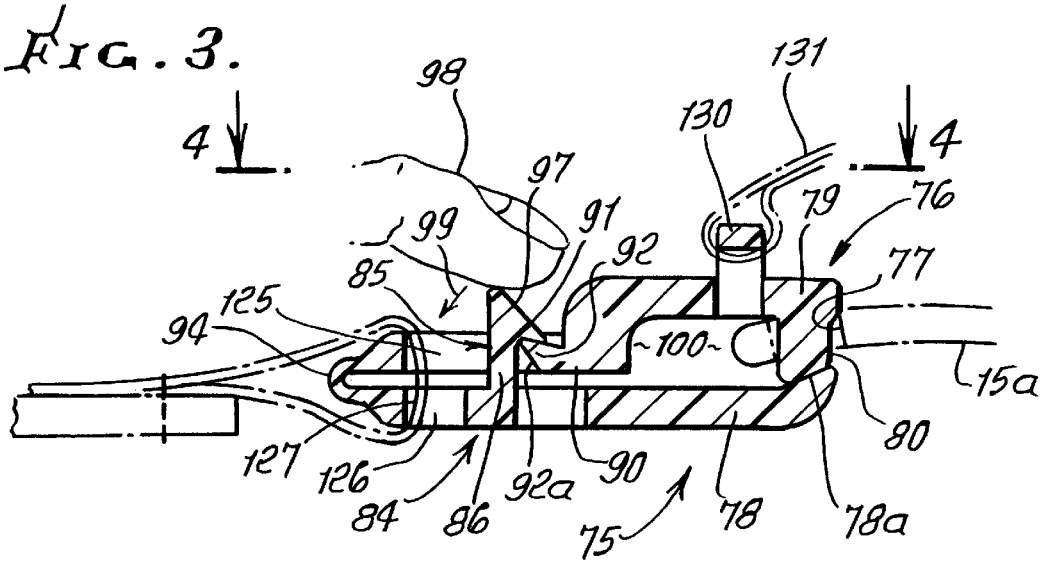
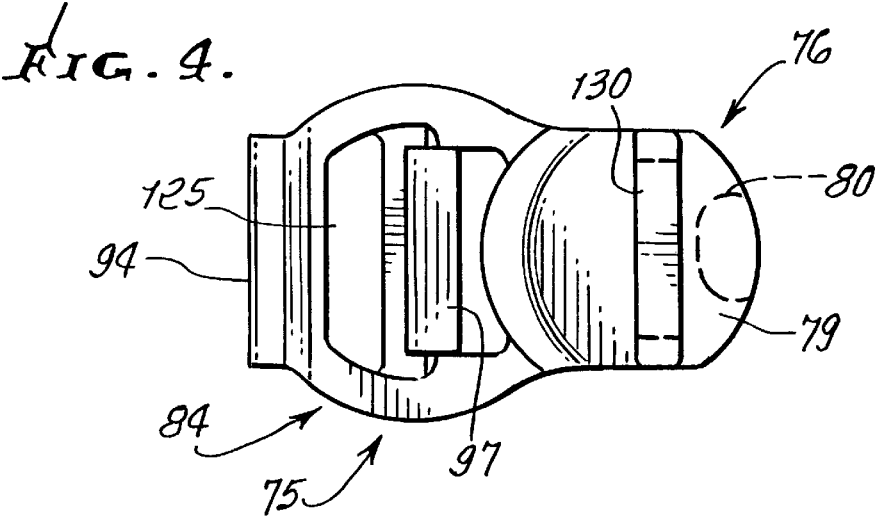
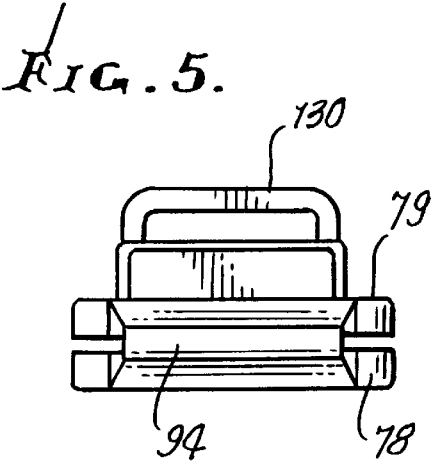

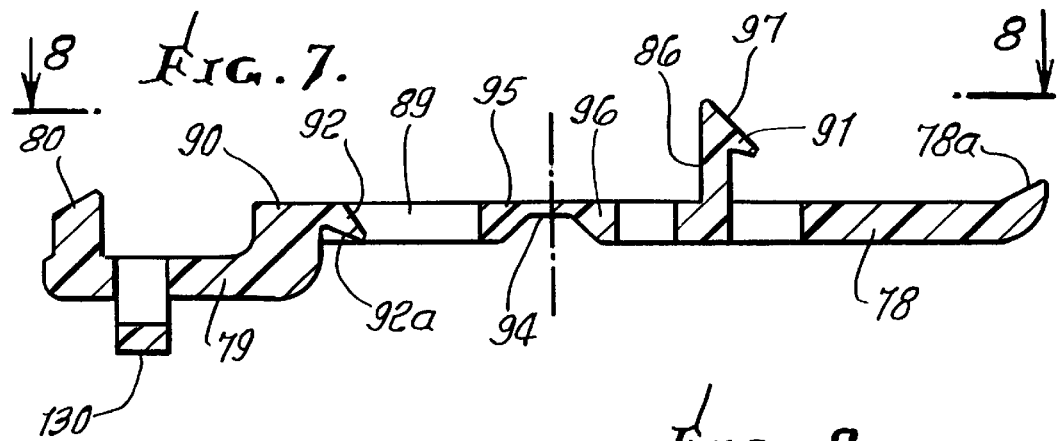
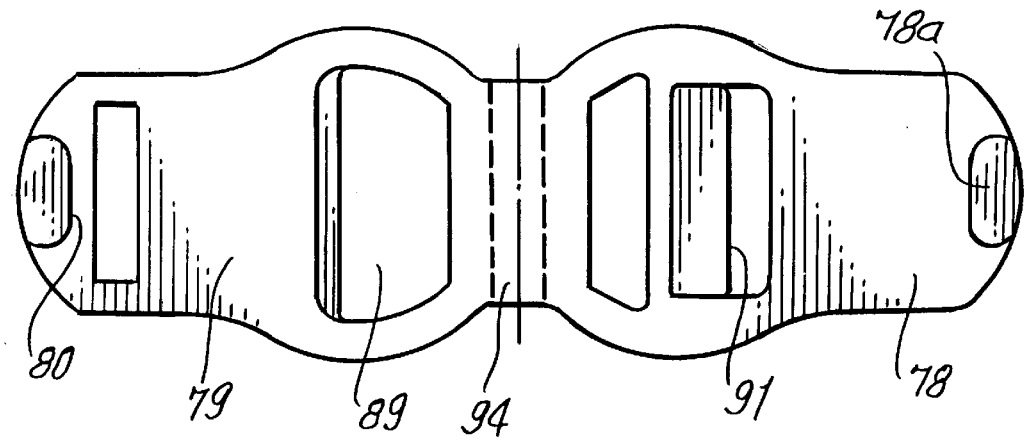
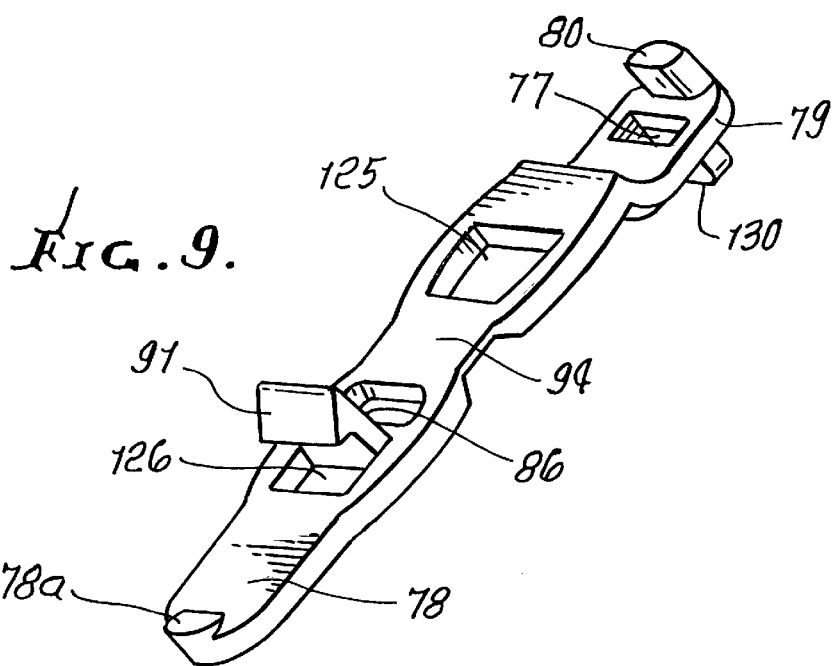

RETENTION SYSTEM FOR ANTI-DISCONNECT APPARATUS AND METHOD, FOR BREATHING SYSTEMS

This application is a continuation-in-part of U.S. patent application Ser. No. 09/080,185 filed May 18, 1998, now pending, which is a continuation-in-part of U.S. patent application Ser. No. 09/010,883 filed Jan. 22, 1998, now pending, both incorporated herein by reference.

This invention relates generally to use of tracheostomy tubes and associated equipment, and more particularly is addressed to the problem of inadvertent disconnection of elements of such equipment, which can lead to unwanted interruption of breathing.

This invention improves upon the highly advantageous apparatus and method disclosed in U.S. Pat. No. 5,282,463 to Hammersley, and incorporated herein by reference.

Tracheostomy plates have been commonly metallic. Clips were used on such plates to anchor the tracheostomy tie band (i.e., "ties"). Older type tracheostomy ties consisted of twill tape that was clumsily tied to each side of the tracheostomy plate, wrapped around the patient's neck, then tied together on the side of the patient's neck.

Later, with the advent of VELCRO™, tracheostomy ties became a little easier to use. Today, tracheostomy ties consist of a variety of materials, such as foam padding, elastic cloth, and wide and narrow materials, to enhance patient comfort. However, all of the tracheostomy ties mentioned above utilize the technique of feeding the tracheostomy tie through the eyelet provided on the tracheostomy tube plate, then fastening in some manner by either tying or using VELCRO™ material.

When the caregiver applies a tracheostomy tie in the conventional manner, the tracheostomy tie is applied under the plate. Some caregivers utilize hemostats or needle holders to attempt to pull the tracheostomy tie through the tie opening, occasionally pinching the patient's skin rather than grabbing the tie. Both of these methods can cause significant discomfort to the patient, while the tracheostomy tube is being manipulated.

The other negative is the time factor. Especially in the current health care market, time is of the essence. If time can be saved in the application of a tracheostomy tie, it would be welcomed. The method and apparatus of this application improve upon the method and apparatus disclosed in Ser. Nos. 09/080,185 and 09/101,883.

SUMMARY OF THE INVENTION

The present invention addresses the problem of securing a tracheostomy tube onto a patient's neck and additionally securing the ventilator breathing circuit onto the tracheostomy plate.

It is a major object of the invention to provide method and means for preventing inadvertent disconnection of breathing system tubing from associated tracheostomy tubes. Basically, use is made of a neck plate usually carried by the tracheostomy tube, and retention apparatus is employed for connecting flexible band means to the tracheostomy neck plate, the neck plate having a wing projecting laterally. The method of the invention includes the steps:

a) providing a first anchor including a first clip connectable to said wing, the band means connectable to the first anchor, b) the first anchor configured to be anchored to the neck plate via the clip and a first opening through the wing, and the first anchor having a first section offset relative to the clip, c) and providing a first lock in association with said section, for holding the anchor in anchored relation to the wing, and releasable to free the first anchor from the wing.

Another object includes provision of a clip that has two arms, the connection method including folding such arm in a clam shell relation to embrace the first wing. Subsequent to such folding, the lock is interacted with one or both arms, to hold them in anchoring relation to the first wing.

A further object includes providing the first anchor with a hinge having portions integral with the two arms, to accommodate such folding, the lock including a tongue integral with one of the arms, an opening integral with the other of the arms, and including passing the tongue through said opening. The tongue typically includes a primary tang spaced from said one arm to pass through the opening during such folding, and including a secondary tang on the other of the arms. The tangs are interconnected in response to said passing of the primary tang through said opening. The tangs may be tapered to facilitate their interengagement and interconnection, and the method includes including interengaging said tangs to connect them.

A yet further object includes providing the tongue with resiliently yieldable and bendable extent to accommodate its deflection to disconnect said tangs, and including flexing said tongue to disconnect them, allowing spreading of said arms and disconnection of the first arm from the neck plate.

An additional object includes providing first adjustable hook and pile connections for retaining the band means adjustably connected relative to said first anchor. The band means may include a first ribbon, to be fitted to said anchor. The anchor may have an offset U-shaped portion, and the first ribbon being fitted about said U-shaped portion.

Further, the method may typically include the provision of a neck plate second wing, there being second band means, and including d) providing a second anchor including a second clip connectable to the second wing, the second band means connectable to the second anchor, e) said second anchor configured to be anchored to the neck plate via said second clip and a second opening through the second wing, and said second anchor having a section offset relative to the second clip, f) and providing a second lock in association with said second section, for holding the second anchor in anchored relation to said second wing, and releasable to free the second anchor from the second wing.

The second anchor, second clip, and second lock may have configurations and modes of operation and use that correspond to those of the first anchor, first clip, and first lock referred to above.

These and other objects and advantages of the invention, as well as the details of an illustrative embodiment, will be more fully understood from the following specification and drawings, in which:

DRAWING DESCRIPTION

FIG. 1 is a top plan view of preferred apparatus incorporating the invention;

FIG. 2 is an elevation taken on lines 2—2 of FIG. 1;

FIG. 3 is an enlarged section taken on lines 3—3 of FIG. 1, and showing the anchor clipped to a tracheostomy neck plate;

FIG. 4 is a top plan view taken on lines 4—4 of FIG. 3;

FIG. 5 is a left end elevational view of the FIG. 4 anchor;

FIG. 6 is a right end elevational view of the FIG. 4 anchor;

FIG. 7 is an elevational view showing the anchor in extended, unfolded condition;

FIG. 8 is a top plan view taken on lines 8—8 of FIG. 7; and

FIG. 9 is a perspective view of the unfolded anchor.

DETAILED DESCRIPTION

In FIGS. 1 and 2, a tracheostomy tube assembly 10 includes an elongated, curved, tube section 11 terminating at an enlarged, tubular head section 12. The assembly 10 also commonly includes a tube portion 11a communicating with head section 12. A neck plate 15 is carried by tube portion 11a, to extend at opposite sides thereof. The plate has wings 15a and 15b which project oppositely, and which narrow in width, in opposite directions 16 and 17. The plate may be oval-shaped as shown.

Wing edges appear at 18–21. Edges 18 and 19 taper in direction 16; and edges 20 and 21 taper in direction 17. The plate also has a face 22 with curvature to fit over a patient's neck 23, when tube section 11 is received through a neck opening and into the trachea. Various other forms of neck plates may be used. A duct, such as an elbow or bend 25 has a leg 27 defining a bore 30 to pass air from a breathing system to the tube 11.

In accordance with the invention, a first anchor is provided to include a first clip connectable to the wing 15a, and band means is provided to be connectable to the first anchor. See for example the illustrated first anchor generally indicated at 75, and having an associated first clip 76 to connect to the wing 15a, as via an opening 77 through that wing. See FIG. 3. The folded clip has a primary plate portion or arm 78 projecting beneath the wing 15a (see FIG. 3), a secondary plate portion or arm 79 projecting above that wing, and a lug 80 integral with 79, and projecting downwardly through opening 77 to engage the projecting and angled surface 78a of the plate 78. Accordingly, in folded condition as shown, the clip positively attaches to the wing 15a, but can easily be released, as by unfolding of the clip, to remove the lug 80 from the opening 77.

The anchor has an associated first section offset relative to the clip, and a first lock is provided in association with that section, for holding the anchor in anchored or clip connected relation to the wing, and being releasable to free the first anchor from the wing. In the example, the anchor first section is indicated at 84 as connected with the plate portion or arm 78 in offset relation to the clip lug 80; and a first lock 85 is associated with section 84 as by integral connection to the latter. The lock includes a tongue 86 integral with projecting arm 78 (see FIG. 3). An opening 89 in a section 90 of arm 79 is positioned to pass the tongue 86, to allow the angled tang 91 on the tongue to cam adjacent angled lower surface 92a of a tang 92 on section 90, whereby the tang 91 is deflected, as the tongue 86 resiliently bends (leftwardly in FIG. 3), and then snaps over the upper surface 92b of tang 92, releasably locking the arms 78 and 79 in folded condition as seen in FIG. 3. An integral hinge 94 interconnects U-shaped offset sections 95 and 96 of the two arms. Release of the lock is achieved by pressing down and leftwardly on the upper lip 97 of the tang 91, as indicated by finger 98 pressure on that lip, in direction 99, allowing tang 91 to slip leftwardly past tang 92, as the arms unfold, and the clip releases from the neck plate.

Note that plate 79 is elevated relative to section 90, in FIG. 3, to provide enlarged space 100 between the plates, when locked, whereby lug 80 can be received downwardly through opening 77 in the neck plate. Also, the tangs are tapered, as shown, to facilitate camming, as described.

FIG. 3 shows registration of openings 125 and 126 through U-shaped arm sections 95 and 96. Those openings pass a tracheostomy tube retention band or ribbon 127. Attachment of the band to the anchor does not require dislodgement of the clip from the plate 15, since the openings 125 and 126 are remote from lug 80, and the band end of the anchor can be lifted clockwise to enable band attachment. FIGS. 1 and 2 show hook and pile connection of the band ends 127a and 127b to widened padding 128 that loops about the wearer's neck.

A U-shaped upstanding grip 130 is provided on plate 79 for retention of a band 131 that attaches the tubing 10 to the neck plate.

A second anchor 140, clip 141, anchor arms 142 and 143, and lock 144 are also seen in FIGS. 1 and 2. These elements have the same construction as the corresponding first elements 75, 76, 78, 79, and 85 described above, and enable attachment by a releasable clip 141 to the neck plate wing 15b, in the same manner as described above, for clip 76.

We claim:

1. The method of connecting flexible first band means to a tracheostomy neck plate, said neck plate having a first wing projecting laterally, the method comprising the steps of:

a) providing a first band means, a tracheostomy neck plate having a central opening for a tracheostomy tube and having at least a first wing projecting laterally of said central opening, said wing having a first opening; and b) providing a first anchor including a first clip comprising two arms pivotally connected by a hinge and connectable to said first wing via said arms, one of said arms carrying a lug and said first anchor having a first section offset relative to said clip for attaching the flexible first band means to the first anchor; and c) providing a first lock on said first section offset for releasably holding the anchor to said first wing and for releasably holding said arms in a folded position; and d) attaching said first anchor to said first wing via said first clip by folding said arms about the hinge, inserting said lug through the first opening and engaging said first lock, said lug protruding through said first opening, and said arms being in a folded position embracing said first wing.

2. The method of claim 1 including providing first adjustable hook and pile connections for retaining said band means adjustably connected relative to said first anchor.

3. The method of connecting flexible first band means to a tracheostomy neck plate, said neck plate having a first wing projecting laterally, the method comprising the steps of:

a) providing a first band means, a tracheostomy neck plate having a central opening for a tracheostomy tube and having at least a first wing projecting laterally of said central opening, said wing having a first opening; and b) providing a first anchor including a first clip comprising two arms pivotally connected by a hinge and connectable to said first wing via said arms, one of said arms carrying a lug and said first anchor having a first section offset relative to said clip for attaching the flexible first band means to the first anchor; and c) providing a first lock on said first section offset for releasably holding the anchor to said first wing and for releasably holding said arms in a folded position, said first lock further including a primary tang and a lock opening respectively at opposing portions of said arms; and d) attaching said first anchor to said first wing via said first clip by folding said arms about the hinge, inserting said lug through the first opening and inserting said primary tang into said lock opening of said first lock, said lug protruding through said first opening and said tang protruding through said lock opening, and said arms being in a folded position embracing said first wing.

4. The method of claim 3 wherein the primary tang is on one arm, there being a secondary tang on the other of the arms, and including interconnecting said tangs in response to said passing of the primary tang through said opening.

5. The combination of claim 4 wherein said tangs are tapered to facilitate their interengagement and interconnection, and including interengaging said tangs to connect them.

6. The method of claim 4 wherein the primary tang includes a tongue having resiliently yieldable and bendable extent to accommodate its deflection to disconnect said tangs, and including flexing said tongue to disconnect them, allowing spreading of said arms and disconnection of the arms from the first wing.

7. The method of claim 3 including providing said band means to include a first ribbon, and fitting said ribbon to said first anchor.

8. The method of claim 7 wherein the first anchor has an offset U-shaped portion, and wherein the first ribbon is fitted about said U-shaped portion.

9. The method of claim 3 wherein the neck plate has a second wing, there being second band means, and including d) providing a second anchor including a second clip connectable to the second wing, the second band means connectable to the second anchor, e) said second anchor configured to be anchored to said neck plate second wing via said second clip and a second opening through the second wing, and said second anchor having a section offset relative to the second clip, f) and providing a second lock in association with said second section, for holding the second anchor in anchored relation to said second wing, and releasable to free the second anchor from the second wing.

* * * * *